United States Patent [19]
Derevyagin et al.

[11] Patent Number: 5,920,010
[45] Date of Patent: Jul. 6, 1999

[54] METHOD OF DETERMINING DEW POINT AND A SUITABLE DEVICE

[75] Inventors: Alexandr Mikhailovich Derevyagin, Sivtsev Vrazhek, 44, ap. 23, 121002m Moscow; Alexandr Georgievich Gubanov, Saratov; Andrei Robertovich Stepanov, Saratov; Sergei Viktorovich Seleznev, Saratov, all of Russian Federation

[73] Assignee: Alexandr Mikhailovich Derevyagin, Moscow, Russian Federation

[21] Appl. No.: 08/981,432

[22] PCT Filed: Jul. 16, 1996

[86] PCT No.: PCT/RU96/00192

§ 371 Date: Dec. 31, 1997

§ 102(e) Date: Dec. 31, 1997

[87] PCT Pub. No.: WO97/04304

PCT Pub. Date: Feb. 6, 1997

[30] Foreign Application Priority Data

Jul. 20, 1995 [RU] Russian Federation ............. 95111606

[51] Int. Cl.⁶ .............................. G01N 7/00; G01N 25/02
[52] U.S. Cl. ..................... 73/335.01; 73/29.01; 374/17
[58] Field of Search ................... 73/29.01, 29.02, 73/335.01, 335.02; 374/16, 17

[56] References Cited

U.S. PATENT DOCUMENTS 2,669,863  2/1954  Shapiro ......................... 374/17
4,040,749  8/1977  David et al. ..................... 356/437
4,894,532  1/1990  Peterson et al. ................. 250/226
5,022,045  6/1991  Elliott ............................. 374/20
5,127,259  7/1992  Kahl et al. ...................... 73/19.1
5,198,094  3/1993  Mettes ........................... 204/430
5,396,325  3/1995  Carome et al. ................. 356/128
5,664,426  9/1997  Lu ................................... 62/93
5,758,968  6/1998  Diebold ........................... 374/17

FOREIGN PATENT DOCUMENTS 593127   11/1975  U.S.S.R. .
1453291   1/1989  U.S.S.R. .
1806361   1/1990  U.S.S.R. .
1744618   6/1992  U.S.S.R. .
2073242  10/1980  United Kingdom .
9201927   2/1992  WIPO .

OTHER PUBLICATIONS

Abstract in Russian and English of SU 593,127.
Abstract in Russian and English of SU 1,806,361.

*Primary Examiner*—Hezron Williams
*Assistant Examiner*—Jay L. Politzer
*Attorney, Agent, or Firm*—Ladas & Parry

[57] ABSTRACT

The proposed method of determining dew point involves directing the gas under investigation onto a cooled section of an optically transparent body through which a luminous flux is allowed to pass and recording fluctuations in the intensity of the luminous flux, the flow-rate of the gas thus directed onto the cooled section being reduced down to zero while its molecular diffusion is preserved. To limit the flow-rate of the gas impinging on the cooled section (1) and reduce contamination of the optically transparent element, the dew point gauge is provided with a sampling tube (10).

6 Claims, 1 Drawing Sheet

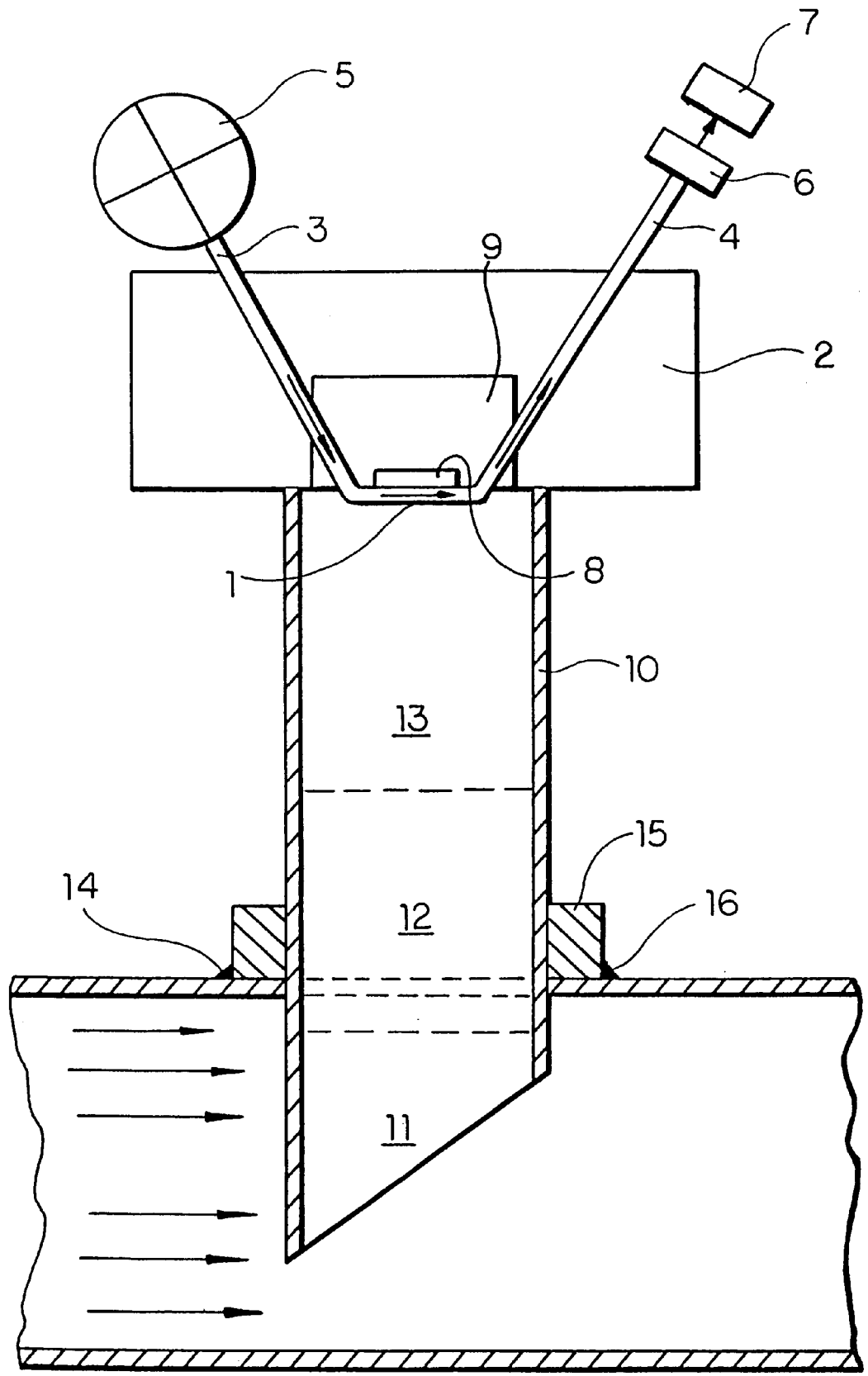

METHOD OF DETERMINING DEW POINT AND A SUITABLE DEVICE

The invention relates to the field of measurement engineering, and more exactly, to the measurement of the moisture content of gases using the dew point method and can be used in dew-point hygrometers and corrosion condensate indicators.

A method of determining dew point is known which consists of directing the gas under investigation onto a cooled section of an optically transparent body through which a luminous flux is allowed to pass and recording fluctuations in the intensity of the luminous flux, by means of which judgment is passed on the onset of the dew point (SU N 593127, 1975), However, when this method is used in dew-point hygrometers, the reliability of measurement is substantially reduced due to contamination of the cooled minor.

A device for determining dew point is known which comprises two light guides having a light-conductive core with a condensation mirror arranged in the gap between the end faces of the light guides, the condensation surface of the mirror being covered with a nonwettable film, a cooling device and a dew point register, wherein the lower portions of the end faces of the light guides are positioned in the plane of the condensation surface (SU No. 1806361, 1990), However, when this device is used, contamination of the mirror with impurities is possible and this reduces the accuracy of measurement.

A method of determining dew point is known which consists of directing the gas under investigation onto a cooled section of an optically transparent body through which a luminous flux is allowed to pass and recording fluctuations in the intensity of the luminous flux, by means of which judgment is passed on the onset of the dew point, and also a dew point gage realized in this method and comprising a cooled section of an optically transparent body, which section is enclosed in a housing and is connected through light guides with radiators and with a converter of luminous flux connected to a register, a cooler and a temperature gage (SU No. 1744618, 1989).

A disadvantage of the known technical solutions is low reliability due to the possible contamination of the optically transparent body with impurities of the gas under investigation, as a result of which an unnecessary layer may be formed which may cause inaccurate measurements and loss of serviceability.

Technical result is to decrease the possible contamination of the optically transparent body.

To provide this result in a method of determining dew point which consists of directing the gas under investigation onto a cooled section of an optically transparent body through which a luminous flux is allowed to pass and recording fluctuations in the intensity of the luminous flux, by means of which judgment is passed on the onset of the dew point, the flow rate of the gas under investigation thus directed onto the cooled section of the optically transparent body is limited to zero while its molecular diffusion to the cooled section of the optically transparent body is preserved, and a dew point gage, comprising the cooled section of the optically transparent body enclosed in a housing and connected through light guides with a radiator and with a converter of luminous flux connected to a register, a cooler and a temperature gage, is provided with a sampling tube, one end of which is secured to the housing around the cooled section of the optically transparent body, while the other end is mounted in the direction of action of gravitational forces.

Furthermore, in accordance with the invention the ratio of the internal cross-sectional area of the tube to the area of the surface of the cooled section of the optically transparent body exceeds 5, while $I^2/S>25$, where I is the length of the sampling tube, S is the internal cross-sectional area of the sampling tube, while the sampling tube is made beveled at the other end and is mounted with the bevel opposing the flow of gas under investigation.

The essence of the invention is that a stagnant zone of the gas under investigation is formed near cooled section of the optically transparent body before passing the luminous flux, the sampling tube is introduced into the device for determining dew point, limited the gas velocity to zero, the fluctuations in the intensity of the luminous flux due to the molecular diffusion of the gas under investigation to the cooled section of the optically transparent body are recorded. These steps allow to decrease considerably the contamination of cooled section of the optically transparent body.

The comparison of the method and the device with the nearest analogs allows to conclude that the invention satisfies the criteria "novelty" and "inventive step".

The results of breadboard tests allow to conclude that the invention satisfies the criteria "industrial applicability".

FIG. 1 shows the construction of the proposed dew point gage.

The method of determining dew point consists of directing the gas under investigation onto a cooled section of an optically transparent body through which a luminous flux is allowed to pass and recording fluctuations in the intensity of the luminous flux, by means of which judgment is passed on the onset of the dew point, A specific feature of the proposed method is that prior to passing the luminous flux through the cooled section of the optically transparent body a stagnant zone of the gas under investigation is formed near that section by limiting the flow rate of the gas thus directed to zero, wherein the molecular diffusion of the gas under investigation to the cooled section of the optically transparent body is preserved.

Due to the creation of a stagnant zone it is not possible for different impurities in the gas to precipitate onto the surface of the cooled section of the optically transparent body, since the gravitational forces act in the opposite direction, and this promotes the preservation of the accuracy with which the dew point is measured, and accordingly enhancement of reliability.

The device (FIG. 1) comprises a cooled section I of an optically transparent body, which section is enclosed in a housing 2 and is connected through light guides 3 and 4 with a radiator 5 and a converter 6 of the luminous flux, respectively, the output of the latter being connected to a register 7. A temperature gage 8 and a cooler 9 are mounted in the housing 2. The device is provided with a sampling tube 10, one end of which is secured to the housing 2 around the cooled section I of the optically transparent body, while the other end is made beveled and is mounted in the direction of action of gravitational forces. The sampling tube 10 is mounted with a bevel opposing the flow of the gas under investigation and has three zones 11, 12, 13 for supplying molecules of the gas under investigation to the cooled section.

For operation the device is mounted in an opening in the pipeline 14 having a flange 15 secured to the pipeline 14 by means of a welded connection 16.

The sampling tube 10 is mounted with a bevel opposing the flow of the gas under investigation, wherein the ratio of the area S of the internal cross section of the sampling tube 10 to the area Sk of the surface of the cooled section I of the optically transparent body exceeds 5, while $I^2/S>25$, where I is the length of the sampling tube 10, S is the internal cross-sectional area of the sampling tube 10.

A bent optical fiber may be used as the cooled section I of the optically transparent body, while an AL-107B type diode is used as the radiator 5.

The device operates in the following manner.

When the device is placed in a medium of the gas under investigation or a mixture of gases, the latter is applied to the condensation surface of the cooled section I of the optically transparent body. If there is no moisture in the medium, a condensate is not formed on the condensation surface, and the luminous flux passes without hindrance from the radiator 5 along the light guide 3 through the cooled section I and the light guide 4 and is applied to the input of the converter 6, but nothing is applied from the output thereof to the register 7, this indicating that there is no condensate, and it does not register the dew point temperature.

Where moisture is present in the gas under investigation, a condensate layer is formed on the cooled section I of the optically transparent body. This condensate layer is made up of finely-divided spherical drops having diameters comparable with the diameter of the core of the used light guide 3. Due to dispersion of the luminous flux by the surfaces of the finely-divided drops of condensate, its intensity sharply drops right down to complete dispersion and nonentry into the light guide 4. Where there is a loss of the luminous flux as a result of dispersion in the cooled section I of the optically transparent body, the converter 6 provides a signal to the register 7 which fixes the onset of the dew point. The temperature of the cooler 9 is determined by the temperature gage 8, the role of which can be played by a thermocouple connected to a galvanometer. The measured dew point temperature may be used to determine the hygrometric parameters of the gas mixture being analyzed or of the automatization of the technological process by which that gas mixture is formed.

The inleakage of the gas under investigation into the sampling tube 10 occurs at the side opposite the bevel, and thus protection against the direct ingress of spray, drops and solid particles into the gage zone is ensured. There are three zones II, 12, 13 in the sampling tube 10 for the supply of molecules of the gas under investigation to section 1. Direct blowing of the sampling tube 10 with a gas flow causes turbulent flows to arise therein in the zone II, and these flows carry molecules of the gas under investigation, possible impurities, aerosols and solid particles into zone 12. Whereby the energy of the whirls is lost and in zone 12 the movement of the gases has a laminar character, the gas being carried into zone 13 by the diffusion exchange of molecules, the presence of which results in filtration of the aerosols and microimpurities present in the gas under investigation, while the aerosols and mechanical admixtures only reach zone 12 of the laminar flows, without penetrating into the diffusion zone 13 because of the gravitational forces acting on them.

If the length of the sampling tube 10 is less than or equal to the sum of the lengths of zones 11, 12, than the turbulent and then laminar flows will carry the aerosols and microimpurities to the condensation surface of the gage and cause contamination. The length of the zones 11 and 12 depends on the dimensions of the sampling tube 10 and the speed at which the gas flows against the bevel of the sampling tube 10. If the sampling tube 10 is cylindrical, then the sum of the lengths of zones 11 and 12 does not exceed five diameters, i.e. if the length of the tube 10 is less than five diameters, then particles and aerosols will contaminate the mirror and cause the device to fail.

If the sampling tube does not have a circular cross section, then the following, limit is valid:

$I^2/S>25$, where I is the length of the sampling tube 10, S is its internal cross-sectional area.

In order to fix the dew point without over-cooling the condensation surface, it is necessary that there be the necessary number of layers of water molecules in the border layer of the gas being analyzed adjacent the surface.

Intensive dispersion of the luminous energy provides such a layer of water molecules which exceeds by three times the wavelength of the luminous flux, Taking into account that the number of water molecules in a continuous monolayer per I $cm^2$ of the condensation surface=$0.87 * 10^{15}$, the diameter of an $H_2O$ molecule is 0.348 nm, and the wavelength of the luminous energy introduced into the optically transparent body is 900 nm, it is not difficult to determine that the necessary number of layers of water molecules for stable fixation of the temperature of condensation is approximately equal to 3000, wherein the number of water molecules which should be in the border layer of the medium being analyzed adjacent to the condensation surface should be $2.6 * 10^{18}$ (with the area of the condensation surface Sk=I $cm^2$ of the cooled section 1 of the optically transparent body).

Condensation of water molecules in the diffusion zone results in diffusion of the same number of molecules from the laminar flow zone, which are then condensed.

Consequently, the necessary number of layers of water molecules in order to attain stable fixation of the temperature of condensation due to diffusion flows are formed on the condensation surface for the time t. The amount of the mass of moisture transferred for the time t by diffusion is:

m=D*dp/dx*S*t, where m is the mass of moisture,

D is the diffusion factor,

S is the area of the surface through which diffusion passes, i.e. the internal cross-sectional area of the sampling tube, t is the transport time, dp/dx is the gradient of density (concentration).

It follows therefrom that the ratio S/Sk should exceed 5. At ratios less than 5 measurement errors will occur.

Thus, high reliability and measurement accuracy are ensured in the proposed method and device due to elimination of contamination.

We claim:

1. A method of determining dew point of a continuous flow of gas under investigation, said method comprising the steps of:

directing the gas under investigation onto a cooled section of an optically transparent body through which a luminous flux is allowed to pass;

recording fluctuations in intensity of the luminous flux;

judging onset of the dew point based on said fluctuations in intensity of the luminous flux;

feeding said gas through a sampling tube having a length L and internal cross-sectional area S related by $L^2/S>25$ which limits the flow rate of the gas under investigation directed onto the cooled section of the optically transparent body.

2. A dew point gage comprising:

A cooled section (1) of an optically transparent body enclosed in a housing (2) and connected through light guides (3,4) with a radiator (5) and with a converter (6) of luminous flux connected to a register (7), a cooler (9), a temperature gage (8) and a sampling tube (10), one end of said sampling tube is secured to the housing (2) around the cooled section (1) of the optically transparent body, and the other end of said sampling tube is mounted in a direction of action of gravitational forces, a ratio of an internal cross-sectional area S of the sampling tube to a surface area of the cooled section of the optically transparent body exceeds 5, and a length L of the sampling tube is related to said internal cross-sectional area S by $L^2/S>25$.

3. A gage according to claim 2, wherein the other end of the sampling tube (10) is beveled and mounted with the bevel oriented toward a direction of flow of the gas under investigation.

4. A dew point gage comprising:

an optically transparent body having first and second opposite ends;

a radiator of luminous flux coupled to said first end;

a converter responsive to said luminous flux coupled to said second end for providing a signal;

a cooling device for cooling a section of said optically transparent body;

a register responsive to said signal for detecting dew on said cooled section;

a temperature gage for indicating a temperature of said cooled section; and a sampling tube having a first end and a second end in fluid communication with a gas for providing fluid communication from said gas to said cooled section, an internal cross-sectional area S of said sampling tube being related to a length L of said sampling tube by the relationship $L^2/S>25$.

5. A gage according to claim 4, wherein a ratio of said internal cross-sectional area S of said sampling tube to a surface area of said cooled section of said optically transparent body exceeds 5.

6. A gage according to claim 4, wherein said second end of said sampling tube is beveled, an oblique line of said second end beveled being oriented toward a direction of flow of said gas under investigation.

* * * * *